(12) United States Patent
Yamasaki

(10) Patent No.: US 11,162,931 B2
(45) Date of Patent: *Nov. 2, 2021

(54) IDENTIFICATION APPARATUS AND IDENTIFICATION SYSTEM

(71) Applicant: KYOCERA Corporation, Kyoto (JP)

(72) Inventor: Hirohide Yamasaki, Yokohama (JP)

(73) Assignee: KYOCERA Corporation, Kyoto (JP)

(*) Notice: Subject to any disclaimer, the term of this patent is extended or adjusted under 35 U.S.C. 154(b) by 587 days.

This patent is subject to a terminal disclaimer.

(21) Appl. No.: 15/409,791

(22) Filed: Jan. 19, 2017

(65) Prior Publication Data

US 2017/0219546 A1  Aug. 3, 2017

(30) Foreign Application Priority Data

Jan. 29, 2016 (JP) .............................. JP2016-016223

(51) Int. Cl.
| | | |
|---|---|---|
| *G01N 33/03* | (2006.01) | |
| *A47J 37/12* | (2006.01) | |
| *G01N 27/12* | (2006.01) | |
| *G01N 29/02* | (2006.01) | |
| *G01N 29/036* | (2006.01) | |
| *A23L 5/10* | (2016.01) | |

(52) U.S. Cl.
CPC .......... *G01N 33/03* (2013.01); *A47J 37/1266* (2013.01); *G01N 27/125* (2013.01); *G01N 29/022* (2013.01); *G01N 29/036* (2013.01); *A23L 5/11* (2016.08); *G01N 2291/02433* (2013.01)

(58) Field of Classification Search
CPC .......... G01N 29/022; A23L 5/11; A47J 37/12
See application file for complete search history.

(56) References Cited

U.S. PATENT DOCUMENTS

| | | | | |
|---|---|---|---|---|
| 2005/0016276 A1* | 1/2005 | Guan | ................... | G01N 29/022 73/579 |
| 2006/0110521 A1* | 5/2006 | Heise | ....................... | A23D 9/00 426/601 |
| 2016/0338540 A1* | 11/2016 | Park | ...................... | G06Q 50/12 |

FOREIGN PATENT DOCUMENTS

| | | |
|---|---|---|
| JP | H06-178731 A | 6/1994 |
| JP | 2004-008255 A | 1/2004 |
| JP | 2015-107439 A | 6/2015 |

* cited by examiner

*Primary Examiner* — Matthew D Krcha

(74) *Attorney, Agent, or Firm* — Studebaker & Brackett PC

(57) ABSTRACT

This identification apparatus is for identifying the degree of degradation of oil and includes a sensor that detects a substance arising from oil contained in an oil tank and a controller that determines the degree of degradation of the oil based on information related to the substance detected by the sensor and the distance from the oil tank containing the oil to the sensor.

8 Claims, 4 Drawing Sheets

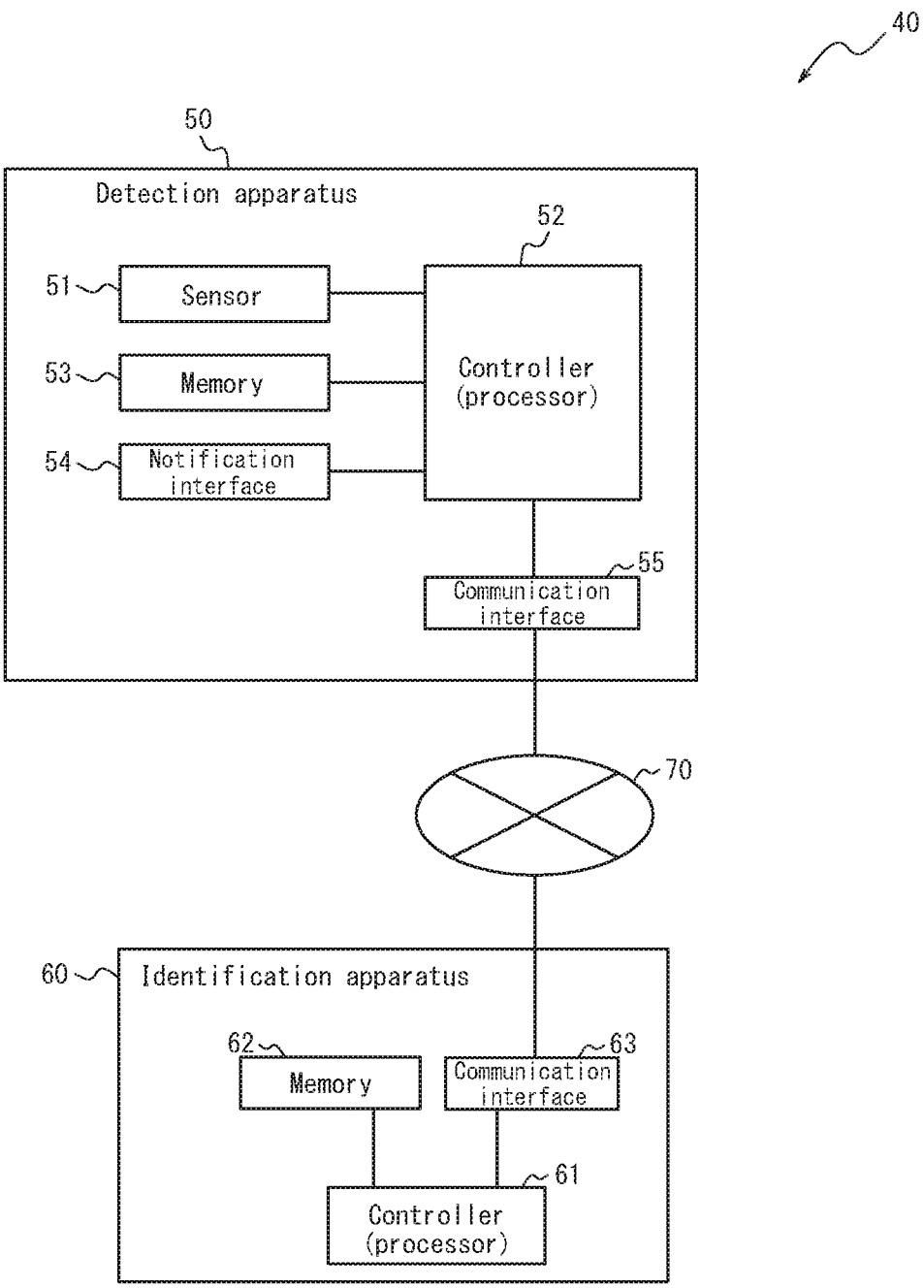

IDENTIFICATION APPARATUS AND IDENTIFICATION SYSTEM

CROSS REFERENCE TO RELATED APPLICATIONS

This application claims priority to and the benefit of Japanese Patent Application No. 2016-016223 filed Jan. 29, 2016, the entire contents of which are incorporated herein by reference.

TECHNICAL FIELD

This disclosure relates to an identification apparatus and an identification system that identify the degree of oil degradation.

BACKGROUND

When cooking oil contained in an oil tank is heated, and food is fried multiple times, the cooking oil gradually degrades. An apparatus that can objectively judge the time for replacement of cooking oil in accordance with the degradation of the cooking oil has been proposed.

SUMMARY

An identification apparatus according to this disclosure is an identification apparatus for identifying a degree of degradation of oil, the identification apparatus including:

a sensor configured to detect a substance arising from oil contained in an oil tank; and a controller configured to determine a degree of degradation of the oil based on information related to the substance detected by the sensor and a distance from the oil tank containing the oil to the sensor.

This disclosure may also be implemented as a system substantially corresponding to the above-described identification apparatus, and such a system is to be understood as included in the scope of this disclosure.

For example, an identification system according to this disclosure includes:

a detection apparatus; and an identification apparatus; such that the detection apparatus includes a sensor configured to detect a substance arising from oil contained in an oil tank and a communication interface configured to transmit information related to the substance detected by the sensor; and the identification apparatus includes a communication interface configured to receive the information over a network and a controller configured to determine a degree of degradation of the oil based on the information and a distance from the oil tank to the sensor.

According to this disclosure, an identification apparatus and an identification system that can identify the degree of oil degradation without attachment to an oil tank can be provided.

BRIEF DESCRIPTION OF THE DRAWINGS

In the accompanying drawings:

FIG. 5 is a functional block diagram schematically illustrating the structure of an identification system according to an embodiment of the disclosure.

DETAILED DESCRIPTION

The following describes embodiments of this disclosure in detail with reference to the drawings.

Embodiment 1

Figure 1:
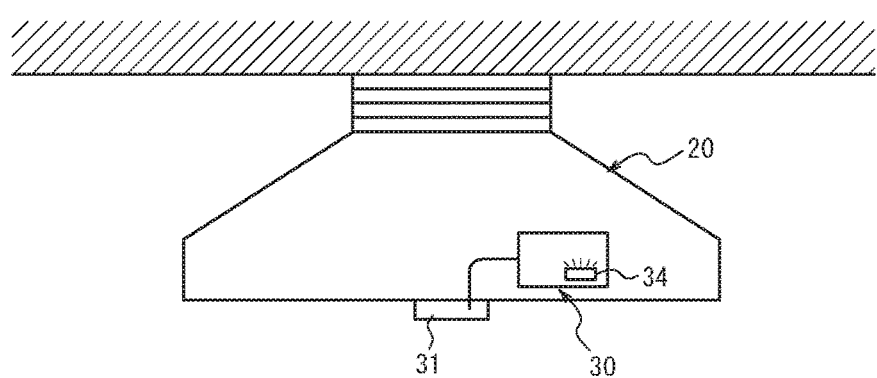
FIG. 1 schematically illustrates an example of placement of an identification apparatus according to an embodiment of the disclosure.
Figure 1:
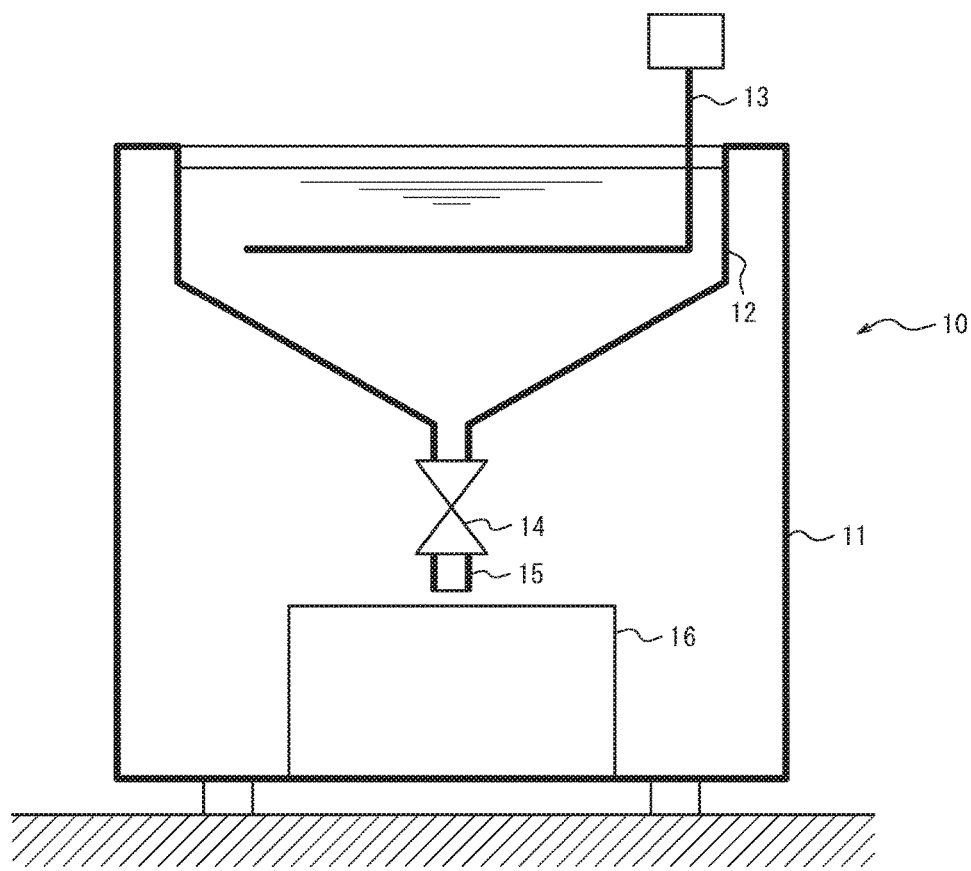

FIG. 1 schematically illustrates an example of placement of an identification apparatus according to Embodiment 1. The following describes the case of the oil being cooking oil, but the oil may be a different type of oil, such as oil for fuel or industrial oil.

In FIG. 1, a fryer 10 for cooking fried food, such as tempura or fried chicken, is installed on the floor. The fryer 10 includes a box-shaped cabinet 11 and an oil tank 12 that contains cooking oil in the upper portion of the cabinet 11. The cooking oil contained inside the oil tank 12 is heated by a heater 13. An oil drain pipe 15 is connected to the bottom of the oil tank 12 via a valve 14. To facilitate oil drainage, the bottom of the oil tank 12 is inclined downwards towards the valve 14 and the oil drain pipe 15. Cooking oil that has degraded is discharged as waste oil by opening the valve 14. A waste oil tank 16 is disposed at the bottom of the oil drain pipe 15 in order to collect the discharged waste oil.

As illustrated in FIG. 1, the oil tank 12 is envisioned as being installed in a large-scale fryer 10 for example used in a convenience store, restaurant, or the like, but the oil tank 12 is not limited to these examples and may be installed in a smaller scale fryer.

Cooking exhaust, such as water vapor and oily smoke, is generated as a result of frying. In order to discharge the generated cooking exhaust sufficiently to the outside, an exhaust fan 20 is installed above the oil tank 12.

Figure 2:
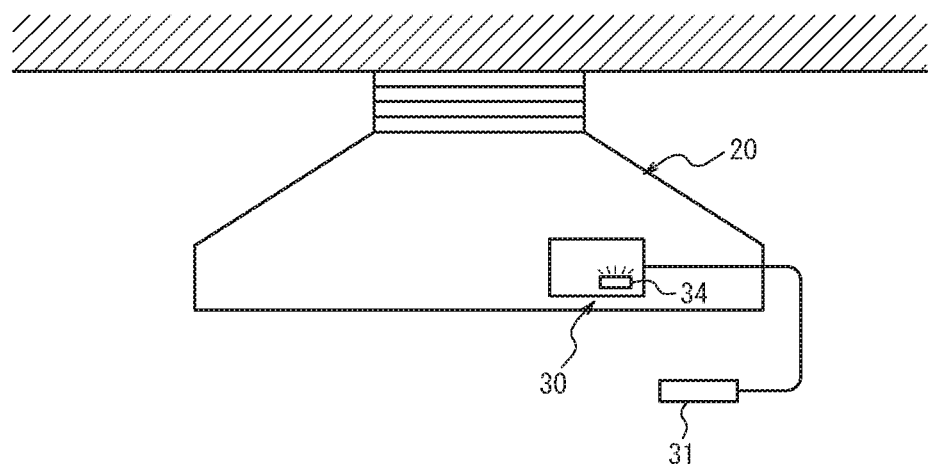
FIG. 2 schematically illustrates another example of placement of the identification apparatus in FIG. 1.

An identification apparatus 30 according to one of the embodiments is, for example, attached to the exhaust fan 20. The identification apparatus 30 comprises a sensor 31. The sensor 31 may, for example, be disposed in the exhaust fan 20. As illustrated in FIG. 2, the sensor 31 may be disposed near the exhaust fan 20 instead. "Near the exhaust fan 20" for example refers to a wall adjacent to the ceiling where the exhaust fan 20 is installed.

Figure 3:
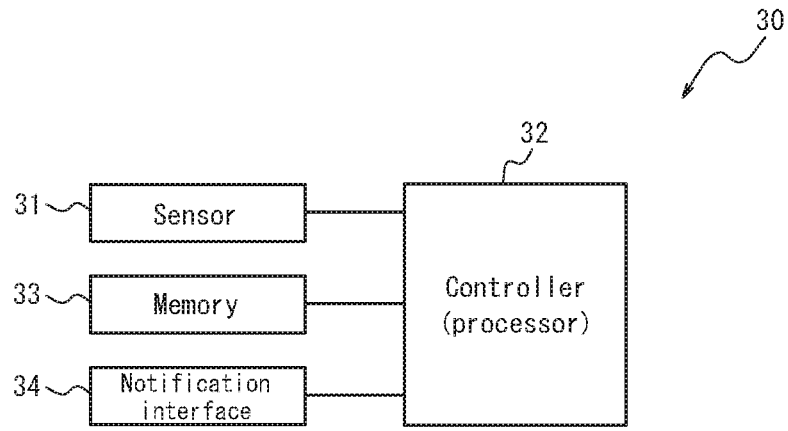
FIG. 3 is a functional block diagram schematically illustrating the structure of the identification apparatus in FIG. 1.

FIG. 3 is a functional block diagram schematically illustrating the structure of the identification apparatus 30 according to this embodiment. The identification apparatus 30 includes the sensor 31, a controller 32, a memory 33, and a notification interface 34.

The sensor 31 detects a substance arising from the cooking oil contained in the oil tank 12. The actual sensor configuring the sensor 31 may be any sensor that can detect the substance and for example detects an odor arising from the cooking oil. In greater detail, the sensor that configures the sensor 31 includes a sensitive membrane and a transducer. The sensitive membrane absorbs gas molecules that are the source of the odor, and the transducer converts the gas molecules in the sensitive membrane into an electrical signal. The sensor 31 transmits the electrical signal converted by the transducer to the controller 32. For example, if the cooking oil degrades, then fatty acids included in the cooking oil decompose. Upon fatty acids decomposing, aldehyde-based or ketone-based substances are generated. In other words, for the sensor 31 to detect the degree of degradation of cooking oil, it suffices for example to provide a sensitive membrane that can detect aldehyde-based or ketone-based substances.

The sensor 31 may, for example, be provided with a Quartz Crystal Microbalance (QCM) type odor sensor that comprises a quartz crystal and a sensitive membrane made of an organic thin film. The QCM type odor sensor detects odor by the resonance frequency of the quartz crystal changing upon gas molecules being adsorbed on the sensitive membrane. The quartz crystal functions as a transducer that converts detection of gas molecules into an electric signal.

The sensor 31 may, for example, be provided with an oxide semiconductor gas sensor. The oxide semiconductor gas sensor detects the gas concentration by a change in the resistance of an oxide semiconductor after gas molecules are adsorbed on the oxide semiconductor. The oxide semiconductor functions as a transducer that converts detection of gas molecules into an electric signal. The sensor 31 may, for example, be provided with an infrared gas sensor, an electrochemical gas sensor, a contact combustion type gas sensor, a biosensor, or the like.

The controller 32 is a processor that, starting with the functional blocks of the identification apparatus 30, controls and manages the identification apparatus 30 overall. The controller 32 is configured using a processor such as a Central Processing Unit (CPU) that executes a program prescribing control procedures. Such a program may, for example, be stored in the memory 33 or in an external storage medium.

The identification apparatus 30 includes at least one processor for providing control and processing capability to perform various functions as described in further detail below. In accordance with various embodiments, the at least one processor may be implemented as a single integrated circuit (IC) or as multiple communicatively coupled IC's and/or discrete circuits. It is appreciated that the at least one processor can be implemented in accordance with various known technologies. In one embodiment, the processor includes one or more circuits or units configurable to perform one or more data computing procedures or processes by executing instructions stored in an associated memory, for example. In other embodiments, the processor may be implemented as firmware (e.g. discrete logic components) configured to perform one or more data computing procedures or processes. In accordance with various embodiments, the processor may include one or more processors, controllers, microprocessors, microcontrollers, application specific integrated circuits (ASICs), digital signal processors, programmable logic devices, field programmable gate arrays, or any combination of these devices or structures, or other known devices and structures, to perform the functions described herein.

The controller 32 executes identification processing by the identification apparatus 30 by controlling the entire identification apparatus 30. For example, the controller 32 activates the sensor 31 based on a predetermined input operation to the identification apparatus 30 by the user of the identification apparatus 30. The sensor 31 activated by the controller 32 starts to detect an odor arising from the cooking oil. The controller 32 acquires information related to the odor detected by the sensor 31 from the sensor 31.

The controller 32 determines the degree of degradation of the cooking oil based, for example, on information related to the odor detected by the sensor 31 during frying and on the distance from the oil tank 12 that contains the cooking oil to the sensor 31. The odor arising from the cooking oil contained in the oil tank 12 changes depending on the distance from the oil tank 12. The controller 32 checks the information related to the odor detected by the sensor 31 against data that, based on distance, indicate the correlation between the odor arising from cooking oil and the degree of degradation of the cooking oil. The data may, for example, be stored in advance in the memory 33. When checking, the controller 32 acquires the data from the memory 33 and executes the processing for checking. As a result, the identification apparatus 30 can identify the degree of degradation of the cooking oil. The information related to the odor detected by the sensor 31 is not limited to an odor arising during frying and may be for an odor arising while not cooking.

The controller 32 may, for example, determine the degree of degradation of the cooking oil based on the outputs of a plurality of sensors and the ratio of the outputs. For example, the controller 32 may determine the degree of degradation of the cooking oil based on characteristic values (output value, time constant, or the like) of the response of a plurality of sensors. For example, the identification apparatus 30 may comprise a plurality of sensors configured to detect ethylene odors, alcohol odors, sulfur odors, ammonia odors, aldehyde odors, ketone odors, and the like. For example, when determining the degree of degradation of cooking oil, the controller 32 may determine that the cooking oil has degraded when, among the outputs of the plurality of sensors, the outputs from sensors that detect aldehyde odors and ketone odors have exceeded a predetermined threshold.

When determining that the degree of degradation of the cooking oil has exceeded a predetermined threshold, the controller 32 controls the notification interface 34 in order to notify the user. This threshold may be set in advance based on data that are stored in advance in the memory 33 and indicate the correlation between an odor arising from the cooking oil and the degree of degradation of the cooking oil. The threshold may be changed appropriately by the user. In either case, the controller 32 stores information related to the threshold in the memory 33.

The controller 32 may determine the degree of degradation of cooking oil using a statistical method, such as principal component analysis, or using a neural network. The controller 32 may generate data by performing a learning process in advance to extract the characteristic values of the response of a plurality of sensors for each degradation state of cooking oil. The controller 32 may store the data after learning in the memory 33. The controller 32 may then determine the degree of degradation of cooking oil based on the degree of matching between the data after learning that are stored in the memory 33 and the data that are detected by the plurality of sensors. Based on newly detected data, the controller 32 may update the data after learning that are stored in the memory 33.

The memory 33 may be configured by a semiconductor memory, a magnetic memory, or the like. The memory 33 stores a variety of information, programs for causing the identification apparatus 30 to operate, and the like. The memory 33 also functions as a working memory. The memory 33 stores data that, based on distance, indicate the correlation between the odor arising from cooking oil and the degree of degradation of the cooking oil. The memory 33 stores data that, for each distance from the oil tank 12 to the sensor 31, indicate the correlation between odor and the degree of degradation of cooking oil. The memory 33 also stores information related to the threshold.

When the controller 32 determines that the degree of degradation of the cooking oil has exceeded a predetermined threshold, the notification interface 34 notifies the user. The notification interface 34 can provide notification for example by a visual method using image, character, or color display, light emission, or the like; an auditory method using audio or the like; or a combination of these methods. In the case of providing notification with a visual method, the notification interface 34 for example is configured by a display device that provides notification by displaying images or characters. As illustrated in FIG. 1, the notification interface 34 may, for example, provide notification by causing an LED or other such light emitting device to emit light. In the case of providing notification with an auditory method, the notification interface 34 for example is configured by a sound generating device, such as a speaker, that provides notification by outputting an alarm sound, audio guidance, or the like. Provision of notification by the notification interface 34 is not limited to a visual or auditory method. Any method by which the user can objectively recognize the time for replacement of cooking oil may be adopted. For example, the notification interface 34 may provide notification with a vibration pattern or the like.

Figure 4:
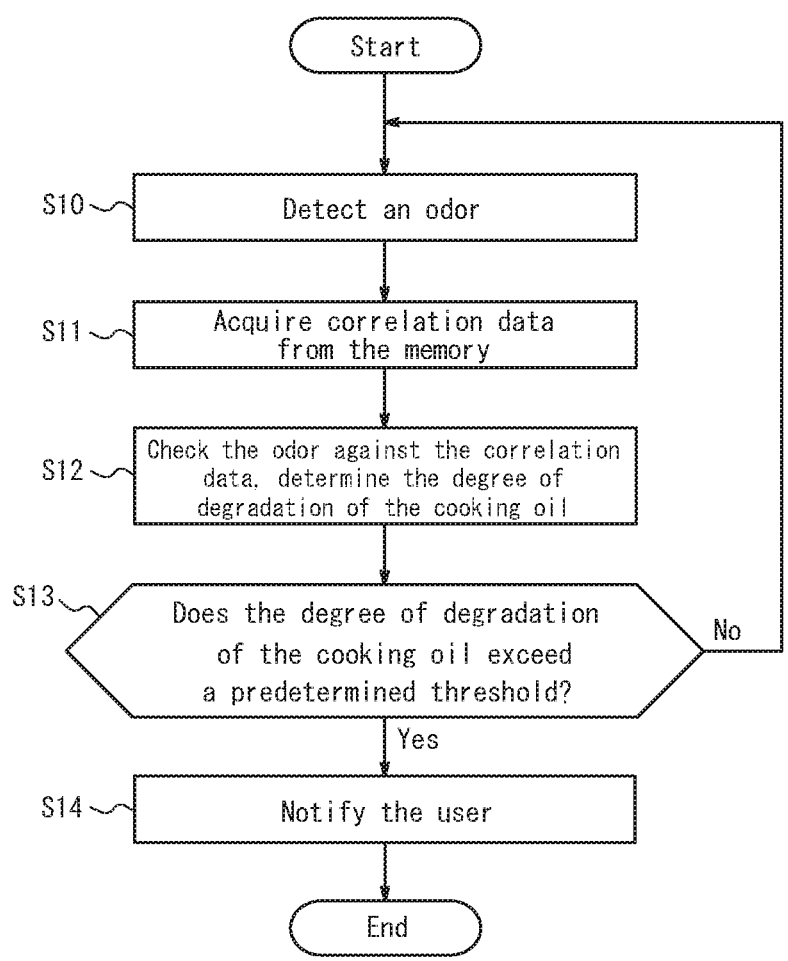
FIG. 4 is a flowchart for identifying the degree of degradation of cooking oil using the identification apparatus in FIG. 1.

FIG. 4 is a flowchart for identifying the degree of degradation of cooking oil using the identification apparatus 30 according to this embodiment. With reference to FIG. 4, an example of the processing executed by the controller 32 when the identification apparatus 30 executes identification processing is described.

First, using an operation button or the like provided on the identification apparatus 30 or outside of the identification apparatus 30, the user performs a predetermined input operation to cause the identification apparatus 30 to start identification processing. For example, the user may input the distance from the oil tank 12 containing the cooking oil to the sensor 31. The distance from the oil tank 12 to the sensor 31 is defined in advance as the distance from a certain position of the oil tank. For example, the distance may be the distance from the oil level of the oil tank or the distance from the upper surface of the oil tank.

After the identification apparatus 30 starts the identification processing, the controller 32 activates the sensor 31 and detects an odor arising from the cooking oil contained in the oil tank 12 (step S10).

Next, from the memory 33, the controller 32 acquires data indicating the correlation between the distance from the oil tank 12 to the sensor 31, the odor, and the degree of degradation of the cooking oil (step S11). The controller 32 acquires data indicating the correlation between odor and the degree of degradation of cooking oil at the distance from the oil tank 12 to the sensor 31.

Next, the controller 32 checks the information related to the odor detected by the sensor 31 against the data, acquired from the memory 33, that indicate the correlation and determines the degree of degradation of the cooking oil (step S12).

Subsequently, the controller 32 determines whether the degree of degradation of the cooking oil exceeds a predetermined threshold (step S13). When the predetermined threshold is exceeded, processing proceeds to step S14. When the predetermined threshold is not exceeded, processing returns to step S10.

When the controller 32 determines that the degree of degradation of the cooking oil has exceeded a predetermined threshold, the controller 32 controls the notification interface 34, and the notification interface 34 notifies the user (step S14). The processing flow then terminates.

With the above processing, the identification apparatus 30 according to this embodiment can identify the degree of degradation of cooking oil without being attached to the oil tank 12.

Furthermore, the identification apparatus 30 according to this embodiment identifies the degree of degradation of the cooking oil based on an odor detected by the sensor 31. Therefore the user can objectively perceive the degree of degradation of the cooking oil. In other words, the user can objectively learn the time for replacement of cooking oil.

The constituent elements including the sensor 31 are disposed on the outside of the oil tank 12 in the identification apparatus 30 according to this embodiment. Therefore the identification apparatus 30 is less prone to being soiled by oil and is easier to clean and manage.

Also, the constituent elements including the sensor 31 are disposed on the outside of the oil tank 12 in the identification apparatus 30 according to this embodiment. Therefore the identification apparatus 30 is less affected by heat, thus reducing the occurrence of failure or malfunction.

Furthermore, the controller 32 determines the degree of degradation of cooking oil based on the distance from the oil tank 12 containing the cooking oil to the sensor 31 in the identification apparatus 30 according to this embodiment. Therefore the degree of degradation of the cooking oil can be identified accurately without dependence on the placement of the sensor 31.

The identification apparatus 30 according to this embodiment has been described as including the sensor 31 that detects odor and the controller 32 that determines the degree of degradation of cooking oil. Different apparatuses that can communicate with each other, however, may respectively include a functional unit that detects odor and a functional unit that determines the degree of degradation of cooking oil. The configuration in such a case is described as Embodiment 2 with reference to FIG. 5.

Embodiment 2

FIG. 5 is a functional block diagram schematically illustrating the structure of an identification system 40 according to Embodiment 2. The identification system 40 includes a detection apparatus 50 and an identification apparatus 60. The detection apparatus 50 and the identification apparatus 60 are connected over a wired or wireless network 70, such as an Internet connection, a Wide Area Network (WAN), or a Local Area Network (LAN), for communication with each other.

The detection apparatus 50 is placed in the same way as the identification apparatus 30 according to Embodiment 1 as illustrated in FIG. 1 or FIG. 2. The detection apparatus 50 includes a sensor 51, a controller 52, a memory 53, a notification interface 54, and a communication interface 55. The functions of the sensor 51, controller 52, memory 53, and notification interface 54 are similar to the functions of the sensor 31, controller 32, memory 33, and notification interface 34 of the identification apparatus 30 illustrated in FIG. 3. Hence, a description thereof is omitted here. The remaining structure, placement, and the like are identical to those of the identification apparatus 30 according to Embodiment 1. Hence, a description thereof is omitted, and the following focuses mainly on the differences from Embodiment 1.

The controller 52 of the detection apparatus 50 according to this embodiment does not determine the degree of degradation of cooking oil. Instead, via the communication interface 55, the controller 52 transmits information related to the odor detected by the sensor 51 to the external identification apparatus 60 over the network 70. Subsequently, the controller 52 acquires information, transmitted over the network 70 from the identification apparatus 60, related to the identified degree of degradation of the cooking oil via the communication interface 55. When the degree of degradation of the cooking oil exceeds a predetermined threshold, the controller 52 controls the notification interface 54 in order to notify the user.

By communicating with the identification apparatus 60 over the network 70, the communication interface 55 transmits and receives a variety of information.

For example, the communication interface 55 transmits information related to the odor detected by the sensor 51 to the identification apparatus 60. When the user appropriately sets the threshold related to the degree of degradation of the cooking oil, the communication interface 55 also transmits information related to the set threshold to the identification apparatus 60. Furthermore, the communication interface 55 also transmits information related to the distance from the oil tank 12 to the sensor 51, as input by the user, to the identification apparatus 60. Various information transmitted from the detection apparatus 50 to the identification apparatus 60 may, for example, be transmitted each time the controller 52 acquires such information or be transmitted when the user performs a predetermined input operation on the detection apparatus 50.

The communication interface 55 acquires information related to the degree of degradation of the cooking oil, as identified by the identification apparatus 60, from the identification apparatus 60 over the network 70.

The identification apparatus 60 may, for example, be configured by a server. The identification apparatus 60 includes a controller 61, a memory 62, and a communication interface 63.

The controller 61 is a processor that, starting with the functional blocks of the identification apparatus 60, controls and manages the identification apparatus 60 overall. The controller 61 is configured using a processor such as a Central Processing Unit (CPU) that executes a program prescribing control procedures. Such a program may, for example, be stored in the memory 62 or in an external storage medium.

The controller 61 determines the degree of degradation of cooking oil based on the various information received from the detection apparatus 50 via the communication interface 63. In greater detail, the controller 61 determines the degree of degradation of the cooking oil based on information related to the odor detected by the sensor 51 and on the distance from the oil tank 12 that contains the cooking oil to the sensor 51. The controller 61 checks the information related to the odor detected by the sensor 51 against data that, based on distance, indicate the correlation between the odor arising from cooking oil and the degree of degradation of the cooking oil. The data may, for example, be stored in advance in the memory 62. When checking, the controller 61 acquires the data from the memory 62 and executes the processing for checking.

Based on information related to a threshold received from the detection apparatus 50 via the communication interface 63, the controller 61 determines whether the degree of degradation of cooking oil has exceeded the threshold. The threshold has been described as being appropriately set in the detection apparatus 50 by the user, but this example is not limiting. This threshold may be set in advance based on data that are stored in advance in the memory 62 and indicate the correlation between an odor arising from the cooking oil and the degree of degradation of the cooking oil.

The controller 61 transmits information related to the determined degree of degradation of cooking oil to the detection apparatus 50 via the communication interface 63 and the network 70.

The memory 62 may be configured by a semiconductor memory, a magnetic memory, or the like. The memory 62 stores a variety of information, programs for causing the identification apparatus 60 to operate, and the like. The memory 62 also functions as a working memory. The memory 62 stores data that, based on distance, indicate the correlation between the odor arising from cooking oil and the degree of degradation of the cooking oil.

By communicating with the detection apparatus 50 over the network 70, the communication interface 63 transmits and receives a variety of information.

For example, the communication interface 63 receives information related to the odor detected by the sensor 51 from the detection apparatus 50. The communication interface 63 also receives information related to the set threshold from the detection apparatus 50. Furthermore, the communication interface 63 also receives information related to the distance from the oil tank 12 to the sensor 51 from the detection apparatus 50.

The communication interface 63 transmits information related to the degree of degradation of the cooking oil, as identified by the identification apparatus 60, to the detection apparatus 50.

With the above processing, the identification system 40 according to this embodiment can identify the degree of degradation of cooking oil without the identification apparatus 60 being attached to the oil tank 12.

Furthermore, the identification system 40 according to this embodiment identifies the degree of degradation of the cooking oil based on an odor detected by the sensor 51. Therefore the user can objectively perceive the degree of degradation of the cooking oil. In other words, the user can objectively learn the time for replacement of cooking oil.

The constituent elements including the sensor 51 are disposed on the outside of the oil tank 12 in the identification system 40 according to this embodiment. Therefore the identification system 40 is less prone to being soiled by oil and is easier to clean and manage.

Furthermore, the controller 61 measures the degree of degradation of cooking oil based on the distance from the oil tank 12 containing the cooking oil to the sensor 51 in the identification system 40 according to this embodiment. Therefore the degree of degradation of the cooking oil can be identified accurately without dependence on the placement of the sensor 51.

It will be clear to a person of ordinary skill in the art that this disclosure may be implemented in ways other than the above embodiments without departing from the spirit or essential features thereof. Accordingly, the above explanation merely provides examples that are in no way limiting. The scope of this disclosure is to be defined by the appended claims, not by the above explanation. Among all changes, those changes that are within the range of equivalents are considered to be included within the scope of this disclosure.

For example, the functions and the like included in the various components and steps may be reordered in any logically consistent way. Furthermore, components or steps may be combined into one or divided.

For example, FIGS. 1 and 2 illustrate structures in which the identification apparatus 30 is attached to the exhaust fan 20, and the sensor 31 is placed on or near the exhaust fan 20, but the placement of the identification apparatus 30 and the sensor 31 is not limited to these examples. The identification apparatus 30 may, for example, be attached to a wall near the ceiling where the exhaust fan 20 is installed or may be placed on the floor. Similarly, the sensor 31 may be placed on a wall closer to the oil tank 12.

For example, in the above embodiments, the sensor 31 has been described as being configured by a sensor that detects an odor arising from the cooking oil, but a sensor other than an odor-detecting sensor may be used. For example, the sensor 31 may be a sensor that detects odorless gas molecules arising from the cooking oil.

The invention claimed is:

1. An identification apparatus for identifying a degree of degradation of oil contained in an oil tank, the identification apparatus comprising:
   a sensor configured to be disposed at a positive distance spaced from the oil tank and to detect gas molecules that are a source of an odor arising from oil contained in the oil tank;
   a controller configured to execute functions of determining a degree of degradation of the oil based on information related to the gas molecules detected by the sensor and the positive distance from the oil tank containing the oil to the sensor and outputting a signal containing the degree of degradation; and
   a memory configured to store data that, based on the positive distance, indicates a correlation between the odor arising from the oil and the degree of degradation of the oil.

2. The identification apparatus of claim 1, further comprising:
   the controller is configured to check the information against the data stored in the memory to determine the degree of degradation of the oil.

3. The identification apparatus of claim 1, further comprising:
   a notification interface; wherein
   the controller is configured to provide, upon making a determination that the degree of degradation of the oil exceeds a predetermined threshold, notification of the determination via the notification interface.

4. The identification apparatus of claim 1, wherein the sensor is disposed in an exhaust fan installed above the oil tank.

5. The identification apparatus of claim 1, wherein the controller receives, via an operation button on the identification apparatus, an input regarding the positive distance, by a user.

6. An identification system for identifying a degree of degradation of oil contained in an oil tank, comprising:
   a detection apparatus; and
   an identification apparatus; wherein
   the detection apparatus comprises
      a sensor configured to be disposed at a positive distance spaced from the oil tank and to detect gas molecules that are a source of an odor arising from oil contained in the oil tank, and
      a communication interface configured to transmit information related to the gas molecules detected by the sensor; and
   the identification apparatus comprises
      a communication interface configured to receive the information over a network,
      a controller configured to execute functions of determining a degree of degradation of the oil based on the information and the positive distance from the oil tank to the sensor and outputting a signal containing the degree of degradation, and
      a memory configured to store data that, based on the positive distance, indicates a correlation between the odor arising from the oil and the degree of degradation of the oil.

7. The identification system of claim 6, wherein
   the controller is configured to check the information against the data stored in the memory to determine the degree of degradation of the oil.

8. The identification system of claim 6, wherein the controller receives, via an operation button on the identification apparatus, an input regarding the positive distance, by a user.

* * * * *